US009290781B2

(12) United States Patent
Yazawa et al.

(10) Patent No.: US 9,290,781 B2
(45) Date of Patent: Mar. 22, 2016

(54) COMPOSITION CONTAINING 2-ACYL-LYSOPHOSPHATIDYLSERINE AND METHOD FOR PRODUCING THE SAME

(75) Inventors: Kazunaga Yazawa, Tokyo (JP); Tomoyuki Susa, Tokyo (JP); Shoji Gotoh, Tokyo (JP); Yasuhito Tashiro, Tokyo (JP); Junichi Kawashima, Tokyo (JP); Shigeyuki Imamura, Izunokuni (JP)

(73) Assignees: National University Corporation Tokyo University of Marine Science and Technology, Tokyo (JP); Meiji Co., Ltd., Tokyo (JP)

( * ) Notice: Subject to any disclaimer, the term of this patent is extended or adjusted under 35 U.S.C. 154(b) by 0 days.

(21) Appl. No.: 13/824,518

(22) PCT Filed: Sep. 26, 2011

(86) PCT No.: PCT/JP2011/071900
§ 371 (c)(1),
(2), (4) Date: Jun. 10, 2013

(87) PCT Pub. No.: WO2012/043481
PCT Pub. Date: Apr. 5, 2012

(65) Prior Publication Data
US 2013/0281404 A1 Oct. 24, 2013

(30) Foreign Application Priority Data
Sep. 30, 2010 (JP) .................. 2010-220880

(51) Int. Cl.
*C12P 13/06* (2006.01)
*A61K 31/685* (2006.01)
*C12P 7/64* (2006.01)

(52) U.S. Cl.
CPC .............. *C12P 13/06* (2013.01); *A61K 31/685* (2013.01); *C12P 7/6481* (2013.01)

(58) Field of Classification Search
CPC ..... C12P 13/96; C12P 7/6481; A61K 31/685; C12N 9/16; C12N 9/20; C12R 1/01
See application file for complete search history.

(56) References Cited

U.S. PATENT DOCUMENTS 5,264,367 A 11/1993 Aalrust et al.
2009/0029428 A1 1/2009 Nishihara et al.

FOREIGN PATENT DOCUMENTS

CN 101437507 A 5/2009
CN 101818179 A 9/2010

(Continued)

OTHER PUBLICATIONS

Ohki et al. "Monovalent cation-induced phospholipid vesicle aggregation: effect of ion bonding", Arch. Biochem. Biophys. 25, 191-200 (1983).*

(Continued)

*Primary Examiner* — Ernst V Arnold
*Assistant Examiner* — Kyung Sook Chang
(74) *Attorney, Agent, or Firm* — Sughrue Mion, PLLC

(57) ABSTRACT

The present invention provides a method for producing a composition containing 2-acyl-lysophosphatidylserine, including (a) a step of obtaining a composition containing phosphatidylserine by allowing phospholipase D to act on a raw material containing phosphatidylcholine in the presence of serine and (b) a step of obtaining a composition containing 2-acyl-lysophosphatidylserine by allowing phospholipase A1 to act on the composition containing phosphatidylserine in the presence of one or more additives selected from the group consisting of the following (I), (II), and (III), in which (I) one or more salts selected from the group consisting of sulfate salts, phosphate salts, nitrate salts, citrate salts, and tartarate salts of monovalent cations, (II) a gum, and (III) an emulsifier.

14 Claims, 1 Drawing Sheet

(56) References Cited

FOREIGN PATENT DOCUMENTS

| JP | 9-121879 | A | | 5/1997 |
|----|----------|---|---|--------|
| JP | 9-227895 | A | | 9/1997 |
| JP | 2002-010796 | A | | 1/2002 |
| JP | 2002-218991 | A | | 8/2002 |
| JP | 2004-532857 | A | | 10/2004 |
| JP | 2006-197842 | A | | 8/2006 |
| JP | 2006-325485 | A | | 12/2006 |
| JP | 2007-28921 | A | | 2/2007 |
| JP | 2009-148244 | A | | 7/2009 |
| WO | WO 0054838 | A1 | * | 9/2000 |
| WO | 2008013215 | A1 | | 1/2008 |

OTHER PUBLICATIONS

JP2002-218991—machine English translation obtained from Espacenet (Jun. 20, 2014).*

JP9-227895—machine English translation obtained from Espacenet (Jun. 20, 2014).*

Hiroshi Sasaki et al., "Ika Yurai Rin Shishitsu kara no Lysophosphatidylserine Chosei", Dai 12 Kai Japanese Society for Marine Biotechnology Taikai, 1-2P-8, May 20, 2009, p. 73.

Masaaki Nishihara et al., "Kaiyo Saikin Yurai Phospholipase A1 no Seishitsu Kento", Japan Oil Chemists' Society Nenkai Koen Yoshishu, vol. 45, Sep. 8, 2006, p. 270, p. 26.

Tomoyuki Koyama et al., "Moritella sp.HFHI0014 Kabu no Yusuru Teion Kasseigata Phospholipase A1 no Anteika Oyobi Kassei Kojo no Kento", Dai 11 Kai Japanese Society for Marine Biotechnology Taikai Koen Yoshishu, May 24, 2008, p. 58, 1-5.

Jun Iwasaki et al., "Moritella sp.HFHI0014 Kabu no Yusuru Phospholipase A1 no Anteika Oyobi Kassei Kojo Kento"; 2008 Nendo The Japanese Society of Fisheries Science Shunki Taikai Koen Yoshishu, Mar. 27, 2008, p. 73, 503.

Jun Iwasaki et al., "Moritella sp. no Sansei sum Rin Shishitsu Bunkai koso no Anteisei Hyoka to Seisei", 2007 Nendo Japan Society for Bioscience, Biotechnology, and Agrochemistry Taikai Koen Yoshishu, 3A16a01, Mar. 5, 2007, p. 210.

International Search Report mailed Nov. 22, 2011 for counterpart International Application No. PCT/JP2011/071900.

English translation of the International Preliminary Report on Patentability and Written Opinion mailed Apr. 18, 2013 for counterpart International Application No. PCT/JP2011/071900.

Guan Wei-ju et al; "Study on Hydrolysis of Soy Lecithin by Phospholipase A1"; Cereals & Oils; vol. 5; Dec. 31, 2006; pp. 6-9.

Junken Aoki et al; "Two pathways for lysophosphatidic acid production"; Biochimica et Biophysica Acta; vol. 1781; Jun. 24, 2008; pp. 513-518.

Kunze, H. et al, "Inhibitors of liver lysosomal acid phospholipase $A_1$", Eur. J. .Biochem., vol. 177, No. 3, 1988, p. 591-595.

* cited by examiner

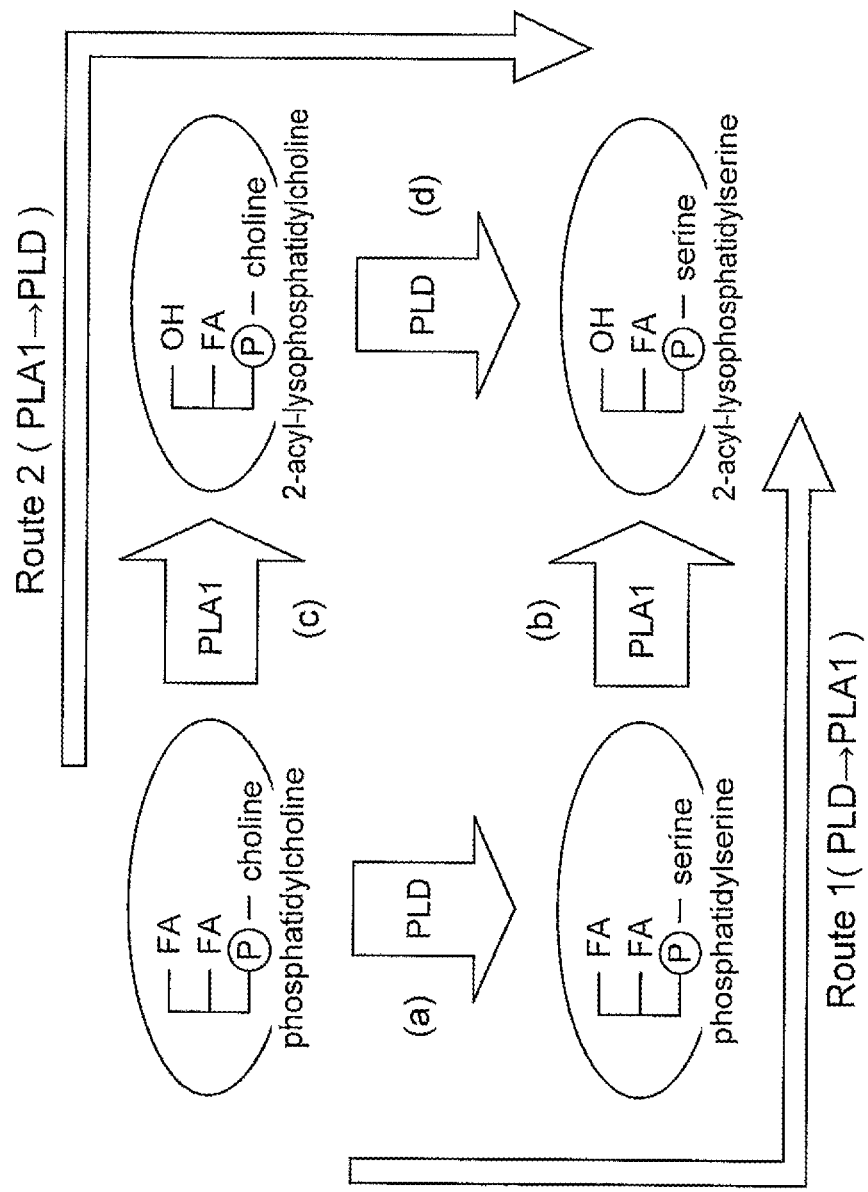

US 9,290,781 B2

COMPOSITION CONTAINING 2-ACYL-LYSOPHOSPHATIDYLSERINE AND METHOD FOR PRODUCING THE SAME

CROSS REFERENCE TO RELATED APPLICATIONS

This application is a National Stage of International Application No. PCT/JP2011/071900 filed Sep. 26, 2011, claiming priority based on Japanese Patent Application No. 2010-220880, filed Sep. 30, 2010, the contents of all of which are incorporated herein by reference in their entirety.

TECHNICAL FIELD

The present invention relates to a composition containing 2-acyl-lysophosphatidylserine and a method for producing the same.

BACKGROUND ART

It is known that, among phospholipids, phosphatidylserine has a physiological function in the brain. As a method for producing phosphatidylserine, a method for obtaining phosphatidylserine by allowing phospholipase D to act on phosphatidylcholine is known (Patent Literature 1 and Patent Literature 2).

On the other hand, a lysophospholipid that is a kind of phospholipid means a phospholipid in which one fatty acid is connected to a glycerin backbone, and it is thought that a lysophospholipid has higher absorption into the body because its molecular weight is smaller than that of a usual phospholipid. Therefore, a lysophosphatidylserine having both structures of a lysophospholipid and phosphatidylserine can be expected to be easily absorbed into the body and have excellent physiologically activity.

Among lysophospholipids, a 2-acyl-lysophospholipid does not have a fatty acid at an sn-1 position and has a fatty acid only at an sn-2 position of the glycerin backbone. It is known that a 2-acyl-lysophospholipid is superior to a 1-acyl-lysophospholipid having a fatty acid only at an sn-1 position thereof in terms of interfacial tension, surface tension, and emulsion stability (for example, Patent Literature 3).

A 2-acyl-lysophospholipid can be obtained by hydrolyzing an ester bond at an sn-1 position of a phospholipid to isolate a fatty acid. Phospholipase A1 is known as an enzyme for hydrolyzing an ester bond at an sn-1 position; Patent Literature 4 discloses a method for converting a phospholipid into a 2-acyl-lysophospholipid by using phospholipase A1 extracted from ovaries of fishes; and Patent Literature 5 discloses the method by using phospholipase A1 produced by microorganisms.

CITATION LIST

Patent Literature

Patent Literature 1: Japanese Patent Application Laid-Open No. 9-121879
Patent Literature 2: Japanese Patent Application Laid-Open No. 2002-218991
Patent Literature 3: Japanese Patent Application Laid-Open No. 9-227895
Patent Literature 4: Japanese Patent Application Laid-Open No. 2006-197842
Patent Literature 5: Japanese Patent Application Laid-Open No. 2006-325485

SUMMARY OF INVENTION

Technical Problem

However, there was a problem in which, in the case where phosphatidylcholine or phosphatidylserine is used as a phospholipid, even if a hydrolysis reaction of a fatty acid at an sn-1 position is performed by phospholipase A1, reactivity of phospholipase A1 with respect to phosphatidylcholine and phosphatidylserine is low and a percentage of conversion of a phospholipid into a lysophospholipid (lysing percentage) is low.

Therefore, it is an object of the present invention to increase the percentage of conversion of the phospholipid into the lysophospholipid (lysing percentage) by phospholipase A1 in producing the composition containing 2-acyl-lysophosphatidylserine.

Solution to Problem

As a result of intensive researches in order to solve the above-described problem, the present inventors have found that, by improving conditions of an enzyme reaction of phospholipase A1, the reactivity of phospholipase A1 with respect to phosphatidylcholine and phosphatidylserine is increased and the lysing percentage can be increased.

That is, the present invention provides a method for producing a composition containing 2-acyl-lysophosphatidylserine, including (a) a step of obtaining a composition containing phosphatidylserine by allowing phospholipase D to act on a raw material containing phosphatidylcholine in the presence of serine and (b) a step of obtaining a composition containing 2-acyl-lysophosphatidylserine by allowing phospholipase A1 to act on the composition containing phosphatidylserine in the presence of one or more additives selected from the group consisting of the following (I), (II), and (III): (I) one or more salts selected from the group consisting of sulfate salts, phosphate salts, nitrate salts, citrate salts, and tartarate salts of monovalent cations, (II) a gum, and (III) an emulsifier.

Moreover, the present invention provides a method for producing a composition containing 2-acyl-lysophosphatidylserine, including (c) a step of obtaining a composition containing 2-acyl-lysophosphatidylcholine by allowing phospholipase A1 to act on a raw material containing phosphatidylcholine in the presence of one or more additives selected from the group consisting of the following (I), (II), and (III): (I) one or more salts selected from the group consisting of sulfate salts, phosphate salts, nitrate salts, citrate salts, and tartarate salts of monovalent cations, (II) a gum, and (III) an emulsifier; and (d) a step of obtaining a composition containing 2-acyl-lysophosphatidylserine by allowing phospholipase D to act on the composition containing 2-acyl-lysophosphatidylcholine in the presence of serine.

According to these methods, by performing the enzyme reaction of phospholipase A1 in the presence of specific additives selected from (I), (II), and (III), the reactivity of phospholipase A1 with respect to phosphatidylcholine and phosphatidylserine is increased and the percentage of conversion of the phospholipid into the lysophospholipid (lysing percentage) can be increased.

Preferably, the additives contain at least (I), and a concentration of the salts of monovalent cations is 0.25 to 2.0 M. By performing the enzyme reaction in the presence of the additives having the concentration of the salts within the range, the lysing percentage can be further increased.

Moreover, preferably, the additives contain at least (I), and the sulfate salts of monovalent cations are ammonium sulfate and/or sodium sulfate. In the case where the additives are ammonium sulfate and/or sodium sulfate, the lysing percentage can be further increased.

Moreover, preferably, the additives contain at least (II), and the gum is one or more selected from the group consisting of xanthan gum, guar gum, tamarind gum, tara gum, gum arabic, and locust bean gum. Furthermore, preferably, the additives contain at least (III), and the emulsifier is one or more selected from the group consisting of sucrose fatty acid ester emulsifiers, polyglycerol fatty acid ester emulsifiers, and polysorbate emulsifiers. By these additives, the lysing percentage can be further increased.

Moreover, preferably, the raw material containing phosphatidylcholine is derived from marine and/or plant. The marine-derived phosphatidylcholine usually contains a highly-unsaturated fatty acid such as docosahexaenoic acid and eicosapentaenoic acid at an sn-2 position, and 2-acyl-lysophosphatidylserine to be obtained is 2-acyl-lysophosphatidylserine in which the highly-unsaturated fatty acid such as docosahexaenoic acid and eicosapentaenoic acid is connected to the sn-2 position thereof. Furthermore, by using plant-derived phosphatidylcholine as the raw material, the lysing percentage can be increased.

Moreover, the present invention provides a composition containing 2-acyl-lysophosphatidylserine, which contains 26 to 51% by mass of a lysophospholipid per solid content. More preferably, 37 to 51% by mass of the lysophospholipid per solid content is contained. Moreover, a percentage of the lysophospholipid in a total phospholipid in the composition containing 2-acyl-lysophosphatidylserine is preferably 40 to 73% by mass, and more preferably 57 to 73% by mass. Furthermore, preferably, 2-acyl-lysophosphatidylserine is 2-acyl-lysophosphatidylserine in which the highly-unsaturated fatty acid is connected to the sn-2 position, and the highly-unsaturated fatty acid is docosahexaenoic acid and/or eicosapentaenoic acid. Since docosahexaenoic acid and eicosapentaenoic acid have physiologically activity such as improvement in memory learning ability, it is thought that 2-acyl-lysophosphatidylserine to which these fatty acids are connected has the same physiologically activity. Such a composition containing 2-acyl-lysophosphatidylserine can be obtained only by the above-described producing method.

Advantageous Effects of Invention

According to the present invention, the percentage of conversion of the phospholipid into the lysophospholipid (lysing percentage) can be increased by phospholipase A1 in producing the composition containing 2-acyl-lysophosphatidylserine.

BRIEF DESCRIPTION OF DRAWINGS

FIG. 1 is a flow diagram illustrating a method for producing a composition containing 2-acyl-lysophosphatidylserine according to the present invention.

DESCRIPTION OF EMBODIMENTS

Hereinafter, a method of the present invention will be described in detail appropriately with reference to the accompanying diagram.

FIG. 1 is a flow diagram illustrating a method for producing a composition containing 2-acyl-lysophosphatidylserine according to the present embodiment. The method according to the present embodiment can be classified roughly into a method of Route 1 and a method of Route 2, which are illustrated in FIG. 1.

Both Route 1 and Route 2 are common in that a raw material containing phosphatidylcholine is used as a raw material; phospholipase A1 (PLA1) and phospholipase D (PLD) are used as enzymes; and a composition containing 2-acyl-lysophosphatidylserine is obtained as a final product. A different point is an order of performing enzyme reactions of PLA1 and PLD. That is, in Route 1, the enzyme reaction of PLD is performed first (step (a)), and PLA1 is made to act on a product produced by the enzyme reaction of PLD (step (b)). Furthermore, in Route 2, the enzyme reaction of PLA1 is performed first (step (c)), and PLD is made to act on a product produced by the enzyme reaction of PLA1 (step (d)). The same raw material may be used and the same enzyme (PLD or PLA1) may be used in Routes 1 and 2 unless otherwise noted in the present description. Hereinafter, regarding the methods of Route 1 and Route 2, the method of Route 1 will be firstly described.

<Regarding Route 1>

The method of Route 1 includes (a) a step of obtaining a composition containing phosphatidylserine by allowing PLD to act on the raw material containing phosphatidylcholine in the presence of serine, and (b) a step of obtaining a composition containing 2-acyl-lysophosphatidylserine by allowing PLA1 to act on the composition containing phosphatidylserine.

Firstly, the step (a) will be described. The raw material containing phosphatidylcholine used in the step (a) is not especially limited as long as it contains lots of phosphatidylcholine. For example, in addition to plant-derived raw materials such as soybeans, rapeseed, linseed, corns, cottonseed, sunflowers, rice germ, barley, oats, and safflowers, which are known as common fat production raw materials, animal-derived raw materials such as fish oil, fish meat, fish roe, fish offal, shellfish meat, shellfish offal, beef, cattle brains, pork, chicken, and egg yolk can be used. In addition, a phospholipid extracted from these raw materials by a conventional method may be used as the raw material containing phosphatidylcholine. As phosphatidylcholine contained in the raw material, phosphatidylcholine in which a highly-unsaturated fatty acid is connected to an sn-2 position is preferable. Although not especially limited, as the highly-unsaturated fatty acid, a carbon number of the unsaturated fatty acid is preferably 16 or more, more preferably 18 or more, and further preferably 20 or more. Moreover, the number of double bonds of the unsaturated fatty acid is preferably 2 or more, more preferably 4 or more, and further preferably 5 or more. Furthermore, the unsaturated fatty acid is preferably an n-3 fatty acid or an n-6 fatty acid, and more preferably an n-3 fatty acid. Specifically, the highly-unsaturated fatty acid is preferably docosahexaenoic acid (DHA) or eicosapentaenoic acid (EPA), and more preferably DHA. Examples of raw materials containing phosphatidylcholine having DHA include marine-derived raw materials extracted from tissue of fish and shellfish such as squids, krill, tunas, bonitos, mackerels, sardines, Pacific sauries, horse mackerels, salmon roe, scallops, and blue mussels, raw materials extracted from tissue of animals such as cattle brains, genetically-modified pigs, and egg yolk, and raw materials extracted from microorganisms such as DHA producing marine bacteria and algae (chlorella or the like). The raw material derived from squids or krill is further preferable because a phospholipid of squids or krill contains lots of phosphatidylcholine in which DHA is connected to an sn-2 position. The above-described raw materials can be used alone or in combination of two or more thereof.

In a producing method of the present invention, the raw material containing phosphatidylcholine can be used by being dissolved or suspended in a solvent suitable for the enzyme reaction of PLD. Examples of such a solvent include chloroform, ether, water, ethyl acetate, petroleum ether, hexane, tetrahydrofuran, pyridine, dichloromethane, and a buffer solution. Among these solvents, it is preferable that at least one selected from the group consisting of chloroform, water, and ether be used. Generally, it is said that ether has an activating effect of phospholipase in an enzyme reaction of a phospholipid. However, in the case where an objective product is used for food application, it is further preferable that water be used because it is harmless to the living body. The above-described solvents can be used alone or appropriately in combination of two or more thereof depending on application or the like of the objective product.

Phospholipase D (PLD) used in the step (a) acts on a phospholipid or a lysophospholipid to cause a phosphatidyl group conversion reaction, and choline connected to a phosphate group in the phospholipid is converted into serine. PLD exists in actinomycetes and plants such as cabbage, spinach, and peanuts, and can be used especially without being limited as long as efficiency of the phosphatidyl group conversion reaction is good. Specific examples of such PLD include Phospholipase D (manufactured by Meito Sangyo Co., Ltd.), Phospholipase D (manufactured by Nagase ChemteX Corporation), Phospholipase D (manufactured by Seikagaku Corporation), Phospholipase D (manufactured by Asahi Kasei Corporation), and PLD (manufactured by Biomol International, L.P.). In the present invention, the examples preferably include Phospholipase D (manufactured by Meito Sangyo Co., Ltd.) and Phospholipase D (manufactured by Asahi Kasei Corporation).

In order to allow PLD to act on the raw material containing phosphatidylcholine in the presence of serine in the step (a), for example, a reaction solution is prepared by dissolving the raw material containing phosphatidylcholine in a reaction solvent; serine is added to the reaction solution; and PLD is added thereto. An additive amount of PLD is preferably 20 to 500 units, more preferably 50 to 200 units, and further preferably 100 units with respect to 1 g of the raw material containing phosphatidylcholine. Although reaction conditions of the enzyme reaction are not especially limited, for example, PLD can be made act within a range of optimum reaction conditions of the enzyme. For example, a reaction temperature is preferably 20 to 70° C., more preferably 30 to 50° C., and further preferably 40° C. Moreover, for example, reaction time is preferably 1 to 48 hours, more preferably 8 to 24 hours, and further preferably 18 hours. For example, the reaction solvent can be selected from among the above-described solvents. Although a reaction of a two-layer system composed of a water-based solvent such as water or a buffer solution and an organic solvent such as ether is preferable in the present invention, in the case where an objective product is used for food application, a reaction system of a water-based solvent such as water or a buffer solution is preferable. For example, a reaction pH is preferably pH of 4.5 to 7.0, more preferably pH of 5.0 to 6.5, and further preferably pH of 5.5. Moreover, an additive amount of serine is preferably 0.5 to 2 g, more preferably 0.7 to 1.5 g, and further preferably 1 g with respect to 1 g of the raw material containing phosphatidylcholine. Furthermore, a reaction activating agent of PLD may be added to the reaction solution. Examples of such a reaction activating agent include calcium chloride. In the case where calcium chloride is used as the reaction activating agent, preferably 0.5 to 2 g, more preferably 0.7 to 1.5 g, and further preferably 1 g of calcium chloride as calcium chloride dehydrate can be used with respect to 1 g of the raw material containing phosphatidyl choline.

After the completion of the enzyme reaction, operations of extraction, condensation, drying and the like are appropriately performed for the reaction solution, and the composition containing phosphatidylserine can be obtained from the reaction solution.

Next, the step (b) will be described. Phospholipase A1 (PLA1) used in the step (b) of the present invention acts on a phospholipid, and an ester bond connected to an sn-1 position in the phospholipid is hydrolyzed to isolate a fatty acid connected to the sn-1 position so that a 2-acyl-lysophospholipid is produced. PLA1 exists in pancreases and livers of animals, ovaries of fishes, microorganisms and the like and can be used especially without being limited as long as a fatty acid is hardly isolated by hydrolyzing an ester bond at an sn-2 position and the 2-acyl-lysophospholipid can be obtained in good yield in the producing method of the present invention. Specific examples of such PLA1 include PLA1 produced by microorganisms of the genus *Aspergillus*, the genus *Pseudomonas*, the genus *Shewanella*, the genus *Pseudoalteromonas*, the genus *Vibrio*, and the genus *Serratia*, and PLA1 extracted from ovaries of fishes such as bonitos, tunas, mackerels, salmons, trouts, and codfishes. The examples preferably include Phospholipase A1 (manufactured by Mitsubishi Chemical Corporation), Lecitase Ultra (registered trade name, manufactured by Novozymes), Lecitase Novo (registered trade name, manufactured by Novozymes), and PLA1 obtained from a culture supernatant of *Pseudomonas* sp. (HFKI0020 strain) described in Japanese Patent Application Laid-Open No. 2006-325485.

Since, if PLA1 is excessively added to a phospholipid, an ester bond of a fatty acid at the sn-2 position in the phospholipid is hydrolyzed in addition to that at the sn-1 position in the phospholipid and the yield of the intended 2-acyl-lysophospholipid may be decreased, an additive amount of PLA1 is preferably 20 to 500 units, more preferably 50 to 200 units, and further preferably 100 units with respect to 1 g of the composition containing phosphatidylserine.

According to the method of the present invention, in the step (b), PLA1 can be allowed to act in the presence of one or more additives selected from the group consisting of the following (I), (II), and (III) to increase a percentage of conversion of a phospholipid into a 2-acyl-lysophospholipid (lysing percentage) by PLA1. (I) is one or more salts selected from the group consisting of sulfate salts, phosphate salts, nitrate salts, citrate salts, and tartarate salts of monovalent cations, (II) is a gum, and (III) is an emulsifier.

The additive (I) is one or more salts selected from the group consisting of sulfate salts, phosphate salts, nitrate salts, citrate salts, and tartarate salts of monovalent cations, and among them, sulfate salts of monovalent cations are especially preferable because the lysing percentage is more increased. In the sulfate salts of monovalent cations, the additive (I) is preferably ammonium sulfate and/or sodium sulfate because the lysing percentage is further increased. For example, in the case where ammonium sulfate is used as the additive (I), a concentration of ammonium sulfate in a reaction system is preferably approximately 0.25 to 2.0 M, and more preferably approximately 1 M. In addition, for example, in the case where sodium sulfate is used as the additive (I), a concentration of sodium sulfate in, a reaction system is preferably approximately 0.25 to 2.0 M, and more preferably approximately 0.75 M. By adding such high-concentration salts, the lysing percentage can be extremely increased.

The additive (II) is a gum. Such gum is preferably one or more selected from the group consisting of xanthan gum, guar gum, tamarind gum, tara gum, gum arabic, and locust bean gum because the lysing percentage is more increased. Moreover, by using the additive (I) together with the additive (II), the lysing percentage can be more increased compared to the case where the additive (I) or the additive (II) is used independently, and thus, the additive (I) is preferably used together with the additive (II). Sulfate salts are preferable as the additive (I) used together with the additive (II), and sodium sulfate or ammonium sulfate is more preferable. In addition, the additive (II) used concurrently is preferably gum arabic.

The additive (III) is an emulsifier. Such emulsifier is preferably one or more selected from the group consisting of sucrose fatty acid ester emulsifiers, polyglycerol fatty acid ester emulsifiers, and polysorbate emulsifiers because the lysing percentage is more increased. In addition, these emulsifiers have preferably an HLB (Hydrophile-Lipophile Balance) value of 10 or more. Moreover, by using the additive (I) together with the additive (III), the lysing percentage can be more increased compared to the case where the additive (I) or the additive (III) is used independently, and thus, the additive (I) is preferably used together with the additive (III). Sulfate salts are preferable as the additive (I) used together with the additive (III), and sodium sulfate or ammonium sulfate is more preferable. In addition, the additive (III) used concurrently is preferably polyglycerol fatty acid ester emulsifiers or polysorbate emulsifiers.

In order to allow PLA1 to act on the composition containing phosphatidylserine in the presence of one or more additives selected from the group consisting of (I), (II), and (III) in the step (b), for example, a reaction solution is prepared by dissolving the composition containing phosphatidylserine obtained by (a) in a reaction solvent; the above-described additives are added to the reaction solution; and PLA1 is added thereto. Although reaction conditions of the enzyme reaction are not especially limited, for example, PLA1 can be made act within a range of optimum reaction conditions of the enzyme. For example, a reaction temperature is preferably 10 to 50° C., and more preferably 30 to 50° C. Regarding reaction time, although a production amount of the 2-acyl-lysophospholipid is increased as reaction time passes, PLA1 causes hydrolysis of the ester bond at the sn-2 position in the phospholipid in addition to that at the sn-1 position in the phospholipid to decrease the yield of the intended 2-acyl-lysophospholipid when the reaction time exceeds appropriate reaction time, and thus, it is preferable that PLA1 be made act within the appropriate reaction time. The appropriate reaction time is 1 to 24 hours, and more preferably 1 to 4 hours. Examples of the reaction solvent include a reaction system of a two-layer system composed of an organic solvent such as ether or ethyl acetate and a water-based solvent such as water or a reaction system of a water-based solvent such as water. Although ether is especially preferably used, in the case where an objective product is used for food application, the reaction system of a water-based solvent such as water is preferable. For example, a reaction pH is preferably pH of 4 to 8, more preferably pH of 4.5 to 6.5, and further preferably pH of 6.5.

After the completion of the enzyme reaction, operations of extraction, condensation, drying and the like are appropriately performed for the reaction solution, and the composition containing 2-acyl-lysophosphatidylserine can be obtained from the reaction solution.

<Regarding Route 2>

Next, the method of Route 2 will be described. The method of Route 2 includes (c) a step of obtaining a composition containing 2-acyl-lysophosphatidylcholine by allowing phospholipase A1 (PLA1) to act on the raw material containing phosphatidylcholine, and (d) a step of obtaining a composition containing 2-acyl-lysophosphatidylserine by allowing phospholipase D (PLD) to act on the composition containing 2-acyl-lysophosphatidylcholine in the presence of serine.

The step (c) is a step of obtaining a 2-acyl-lysophospholipid from a phospholipid by PLA1, and the same reaction conditions as the step (b) can be used. That is, according to the method of the present invention, in the step (c), by allowing PLA1 to act in the presence of one or more additives selected from the group consisting of (I), (II), and (III), the percentage of conversion of the phospholipid into the lysophospholipid (lysing percentage) can be increased. As PLA1, the examples described in the explanation of the step (b) can be used, and the additives (I), (II), and (III) are the additives (I), (II), and (III) described in the explanation of the step (b). In addition, as the raw material containing phosphatidylcholine, the raw materials described in the explanation of the step (a) can be used. After the completion of the enzyme reaction, operations of extraction, condensation, drying and the like are appropriately performed for the reaction solution, and the composition containing 2-acyl-lysophosphatidylcholine can be obtained from the reaction solution.

The step (d) is a step of converting choline connected to a phosphate group in 2-acyl-lysophosphatidylcholine obtained by the step (c) into serine by the action of PLD, and the same reaction conditions as the step (a) can be used. For example, as PLD, serine, and the reaction activating agent, the examples described in the explanation of the step (a) can be used respectively. After the completion of the enzyme reaction, operations of extraction, condensation, drying and the like are appropriately performed for the reaction solution, and the composition containing 2-acyl-lysophosphatidylserine can be obtained from the reaction solution.

According to the method of the present invention, by using either method of Route 1 or Route 2, the reactivity of PLA1 with respect to phosphatidylcholine and phosphatidylserine can be increased; the percentage of conversion of the phospholipid into the lysophospholipid (lysing percentage) can be increased; and the intended 2-acyl-lysophosphatidylserine can be obtained in good yield. It is to be noted that "lysing percentage" in the present description can be determined by methods described in Examples.

In the method of the present invention, either method of Route 1 or Route 2 may be used to obtain the composition containing 2-acyl-lysophosphatidylserine.

<Regarding 2-acyl-lysophosphatidylserine>

It is preferable that the composition containing 2-acyl-lysophosphatidylserine obtained by the above methods have a high content of a lysophospholipid per solid content. This is because, among lipids, a lysophospholipid has an excellent physiologically active function. For example, 26 to 51% by mass, and more preferably 37 to 51% by mass, of the lysophospholipid per solid content is contained. Furthermore, a percentage of the lysophospholipid in the total phospholipid in the composition is preferably high. For example, the percentage of the lysophospholipid in the total phospholipid is preferably 40 to 73% by mass, and more preferably 57 to 73% by mass. It is to be noted that the above-described "the percentage of the lysophospholipid in the total phospholipid" can be determined by (lysophospholipid content)/(total phospholipid content)×100%. "The total phospholipid content"

and "the lysophospholipid content" can be respectively determined by methods described in Examples.

Furthermore, it is preferable that 2-acyl-lysophosphatidylserine contained in the composition contain a fatty acid having a specific physiologically active function. Examples of the fatty acid having a specific physiologically active function include a highly-unsaturated fatty acid. The highly-unsaturated fatty acid functions as a physiologically active substance in the body. The highly-unsaturated fatty acid is preferably docosahexaenoic acid (DHA) and/or eicosapentaenoic acid (EPA). It is known that these highly-unsaturated fatty acids respectively have a physiologically active function such as improvement in memory learning ability. Among these highly-unsaturated fatty acids, DHA, is preferable. DHA is contained a lot in seafood such as fish and shellfish, and is a highly-unsaturated fatty acid which particularly excels in a physiologically active function.

The lysophospholipid such as 2-acyl-lysophosphatidylserine contained in the composition provided by the method of the present invention functions as a physiologically active substance. Therefore, by blending the composition obtained by the method of the present invention, food and drink and medical products to which a physiologically active function is imparted can be provided. In this case, since the above-described composition obtained by the method of the present invention has a high content in the lysophospholipid, a high effect can be obtained even if a blending amount of the composition is small. Moreover, in the case where the highly-unsaturated fatty acid such as DHA and EPA is connected to the sn-2 position of 2-acyl-lysophosphatidylserine contained in the composition, food and drink and medical products to which an excellent physiologically active function such as improvement in memory learning ability is imparted can be provided.

EXAMPLES

Hereinafter, the present invention will be concretely described with reference to Examples, but is not limited to these Examples. It is to be noted that, in Examples, "%" means "w/v %" unless otherwise described.

Analysis methods of a total phospholipid content, a lysophospholipid content, and a lysing percentage, which are described below, are values obtained by the following measurement methods.

1. <Analysis Method of Total Phospholipid Content>

The total phospholipid content was determined by the following method.

(A): Absorbance of Sample Solution at Measurement Wavelength of 500 nm (B): Absorbance of Total Phospholipid Standard Solution at Measurement Wavelength, of 500 nm $$\text{Total Phospholipid Content(mass \%)}=(A)/(B)\times 100 \text{ (mass \%)}$$

A solution in which a sample is dissolved in methanol hydrochloride such that a concentration is 20 mg/mL was heated at 65° C. for 30 minutes. After bringing back to room temperature, equivalent amount of water, and then, equivalent amount of hexane were added to the solution and the solution was sufficiently stirred and mixed. After centrifuging the solution (3000 rpm, 5 minutes), 10 μL of a lower layer of the solution was added to 1.0 mL of an enzyme coloring reagent for analyzing the total phospholipid, which has the following composition. After the solution was colored at 37° C. for 20 minutes, absorbance (A) at a measurement wavelength of 500 nm was measured.

Composition of Enzyme Coloring Reagent for Analyzing Total Phospholipid;
 0.1 M Tris Hydrochloride (pH 8.0),
 0.2% Triton X-100,
 10 mM Calcium Chloride,
 0.1% Phenol,
 0.1% 4-Aminoantipyrine,
 0.2 U/mL Glycerophosphorylcholinephosphodiesterase,
 5 U/mL Glycerophosphate Oxidase,
 10 U/mL Peroxidase.

On the other hand, a total phospholipid standard solution (a solution in which egg yolk phosphatidylcholine manufactured by AVT is dissolved in methanol hydrochloride such that a concentration is 20 mg/mL) was used as a sample; the same operations as described above were performed; and absorbance (B) was measured. The total phospholipid content was determined by (A)/(B)×100 (mass %).

2. <Analysis Method of Lysophospholipid Content>

The lysophospholipid content was determined by the following method.

(C): Absorbance of Sample Solution at Measurement Wavelength of 500 nm (D): Absorbance of Lysophospholipid Standard Solution at Measurement Wavelength of 500 nm $$\text{Lysophospholipid Content(mass \%)}=(C)/(D)\times 100 \text{ (mass \%)}$$

10 μL of a solution in which a sample is dissolved in 2% Triton X-100 such that a concentration is 10 mg/mL was added to 1.0 mL of an enzyme coloring reagent for analyzing the lysophospholipid, which has the following composition; the solution was reacted at 37° C. for 20 minutes; and then, absorbance (C) at a measurement wavelength of 500 nm was measured.

On the other hand, a lysophospholipid standard solution (a solution in which egg yolk lysophosphatidylcholine manufactured by AVT is dissolved in 2% Triton X-100 such that a concentration is 10 mg/mL) was used as a sample; the same operations as described above were performed; and absorbance (D) was measured. The lysophospholipid content was determined by (C)/(D)×100 (mass %).

Composition of Enzyme Coloring Reagent for Analyzing Lysophospholipid;
 0.1 M Tris Hydrochloride (pH 8.0),
 0.2% Triton X-100,
 10 mM Calcium Chloride,
 0.1% Phenol,
 0.1% 4-Aminoantipyrine,
 4 U/mL Lysophospholipase,
 0.2 U/mL Glycerophosphorylcholinephosphodiesterase,
 5 U/mL Glycerophosphate Oxidase,
 10 U/mL Peroxidase.

3. <Analysis Method of Lysing Percentage>

The lysing percentage was determined by the following method.

(E): Absorbance of Lysophospholipid in Solution after PLA1 Reaction at Measurement Wavelength of 500 nm (F): Absorbance of Total Phospholipid in Raw Material at Measurement Wavelength of 500 nm $$\text{Lysing Percentage(mol \%)}=(E)/(F)\times 100 \text{(mol \%)}$$

5 μL of phospholipase A1 (1000 units/mL) aqueous solution was added to 1.0 mL of a 0.1 M acetate buffer (pH 5.5) in which a sample phospholipid is dissolved such that a concentration is 5%, and the mixture was stirred at 40° C. for 4 hours to cause a lysing reaction. After the reaction, 1.0 mL of hexane was added to perform extraction of a phospholipid. 10

µL of a hexane phase was collected and hexane was removed under reduced pressure. 1.0 mL of the above-described enzyme coloring reagent for analyzing the lysophospholipid was added thereto, the reaction was performed at 37° C. for 20 minutes, and absorbance (E) at a measurement wavelength of 500 nm was measured. The absorbance (E) is proportional to a molar concentration of the lysophospholipid.

On the other hand, 500 µL of the hexane phase was transferred to a test tube, and hexane was distilled away under reduced pressure. 0.75 mL of methanol hydrochloride was added thereto, and the reaction was performed at 65° C. for 30 minutes. After bringing back to room temperature, 0.75 mL of water, and then, 0.75 mL of hexane were added to extract a lipid constituent. 30 µL of a lower layer was added to 1.0 mL of the above-described enzyme coloring reagent for analyzing the total phospholipid; the solution was colored at 37° C. for 20 minutes; and absorbance (F) at a measurement wavelength of 500 nm was measured. The absorbance (F) is proportional to a molar concentration of the total phospholipid. The lysing percentage was determined by (E)/(F)×100 (mol %).

Example 1

Preparation of Phosphatidylserine 450 mL of purified water was added to 50 g of a phospholipid (krill phosphatidylcholine) obtained by acetone treatment of 100 g of krill oil, and the solution was stirred. 80 mL of 1 M acetate buffer (pH 5.5), 35 g of calcium chloride, and 68 g of serine were sequentially added thereto and dissolved therein. After 200 mL of purified water was added to the solution, 5000 units of Phospholipase D (manufactured by Meito Sangyo Co., Ltd.) was added, and the reaction was performed, while stirring, at 40° C. for 18 hours. 800 mL of hexane was added to the reaction solution, and extraction was performed at room temperature for 30 minutes. A hexane phase was collected and dried under reduced pressure by a rotary evaporator to obtain 42 g of solid matter containing phosphatidylserine (krill phosphatidylserine).

Example 2

Effect of Sulfate Salt on Enzyme Reaction by PLA1

5 µL of phospholipase A1 (1000 units/mL) aqueous solution was added to 1.0 mL of a reaction solution prepared from 0.1 M acetate buffer (pH 5.5), 5% gum arabic or without addition of gum arabic, 5% solid matter containing phosphatidylserine prepared in Example 1, and 1 M various salts, and the mixture was stirred at 40° C. for 4 hours to cause an enzyme reaction. After the completion of the reaction, the lysing percentages were measured in accordance with the above-described 3. <Analysis Method of Lysing Percentage>. The results are shown in Table 1. In the case where gum arabic is not added, the lysing percentages were high in the presence of ammonium sulfate (($NH_4$)$_2SO_4$), sodium sulfate ($Na_2SO_4$), monosodium phosphate ($NaH_2PO_4$), sodium nitrate ($NaNO_3$), trisodium citrate ($Na_3$-Citrate), and disodium tartarate ($Na_2$-Tartarate), and a facilitation effect of these salts on the enzyme reaction of PLA1 was recognized. In the case where gum arabic is added, the lysing percentages were higher especially in the presence of ammonium sulfate and sodium sulfate, and an excellent enzyme reaction facilitation effect was recognized.

TABLE 1

| | lysing percentage (%) | |
|---|---|---|
| salts | without addition of gum arabic | addition of 5% gum arabic |
| without addition | 37.2 | 42.5 |
| 1M ($NH_4$)$_2SO_4$ | 67.1 | 79.1 |
| 1M $Na_2SO_4$ | 66.7 | 78.2 |
| 1M $Mg_2SO_4$ | — | 47.2 |
| 1M $NaH_2PO_4$ | 46.6 | 50.8 |
| 1M $NaNO_3$ | 42.9 | 46.4 |
| 1M $Na_3$-Citrate | 62.8 | 68.7 |
| 1M $Na_2$-Tartarate | 63.4 | 67.3 |
| 1M NaCl | — | 37.1 |
| 1M KCl | — | 22.3 |
| 1M $NH_4Cl$ | — | 38.0 |
| 1M $Na_4P_2O_7$ | — | 32.4 |
| 1M $Na_2CO_3$ | — | 26.1 |
| 1M $NaHCO_3$ | — | 29.1 |

<Effect of Salt Concentration of Sulfate Salt on Lysing Reaction by PLA1>

An effect of a salt concentration on the lysing percentage was examined with respect to ammonium sulfate and sodium sulfate in which enzyme reaction facilitation effects were high. The enzyme reactions by PLA1 were performed with ammonium sulfate or sodium sulfate at salt concentrations shown in Table 2 existing together with 5% gum arabic. The results are shown in Table 2. In both ammonium sulfate and sodium sulfate, maximum enzyme reaction facilitation effects were obtained at a concentration of approximately 0.75 to 1.0 M.

TABLE 2

| | lysing percentage (%) addition of 5% gum arabic | |
|---|---|---|
| concentration salt | ($NH_4$)$_2SO_4$ | $Na_2SO_4$ |
| 0.25M | 61.2 | 50.2 |
| 0.5M | 74.4 | 75.5 |
| 0.75M | 79.1 | 80.1 |
| 1.0M | 81.5 | 79.3 |
| 1.5M | 73.3 | 74.1 |
| 2.0M | 67.1 | 61.8 |

Example 3

<Effect of Gums on Enzyme Reaction by PLA1> An effect of various gums on the lysing percentage without addition of sulfate salts or in the presence of sulfate salts was examined. 5 µL of phospholipase A1 (1000 units/mL) aqueous solution was added to 1.0 mL of a reaction solution prepared from 0.1 M acetate buffer (pH 5.5), 1 M sodium sulfate or without addition of sodium sulfate, 5% solid matter containing phosphatidylserine prepared in. Example 1, and each of gums at concentrations shown in Table 3, and the mixture was stirred at 40° C. for 4 hours to cause an enzyme reaction. After the completion of the reaction, the lysing percentages were measured in accordance with the above-described 3. <Analysis Method of Lysing Percentage>. As shown in Table 3, an enzyme reaction facilitation effect was observed in xanthan gum, guar gum, tamarind gum, tara gum, gum arabic, locust bean gum and the like, and a higher enzyme reaction facilitation effect was recognized when existing together with sulfate salts.

TABLE 3

| gums | trade name | concentration | lysing percentage (%) without addition of $(NH_4)_2SO_4$ | lysing percentage (%) addition of 1M $(NH_4)_2SO_4$ |
|---|---|---|---|---|
| without addition | | | 38.0 | 68.9 |
| xanthan gum | Echo Gum F | 0.5% | 29.9 | 57.7 |
| | | 0.1% | 51.6 | 74.5 |
| | San-Ace NXG-S | 0.5% | 54.7 | 49.4 |
| | | 0.1% | 54.8 | 75.5 |
| guar gum | Neosoft G | 1% | 28.7 | 65.9 |
| | | 0.5% | 45.3 | 66.3 |
| | Bistop D-20 | 1% | — | 81.5 |
| | | 0.5% | 30.4 | 51.1 |
| | | 0.1% | 43.4 | 79.6 |
| tamarind gum | Neosoft TA | 5% | 28.9 | 68.7 |
| | | 3% | 48.9 | 77.3 |
| | | 1% | — | 70.0 |
| | Bistop D-2032 | 3% | — | 72.2 |
| | | 1% | — | 75.4 |
| tara gum | Neosoft T | 0.5% | 48.7 | 78.3 |
| | | 0.25% | 43.7 | 62.4 |
| gum arabic | | 10% | — | 78.8 |
| | | 7.5% | — | 80.7 |
| | | 5% | 47.2 | 80.6 |
| | | 3% | — | 76.1 |
| | | 1% | — | 73.1 |
| locust bean gum | Neosoft L-5 | 1% | — | 68.0 |
| | Bistop-171 | 1% | — | 74.4 |
| tragacanth gum | | 1% | 23.2 | 55.7 |
| | | 0.5% | 31.2 | 59.9 |
| ghatti gum | Ghatti Gum SD | 1% | — | 32.2 |

Example 4

Effect of Emulsifier on Enzyme Reaction by PLA1

An effect of various emulsifiers on the lysing percentage without addition of sulfate salts and in the presence of sulfate salts was examined. 5 µL of phospholipase A1 (1000 units/mL) aqueous solution was added to 1.0 mL of a reaction solution prepared from 0.1 M acetate buffer (pH 5.5), 1 M sodium sulfate or without addition of sodium sulfate, 5% solid matter containing phosphatidylserine prepared in Example 1, and each of emulsifiers at concentrations shown in Table 4, and the mixture was stirred at 40° C. for 4 hours to cause an enzyme reaction. After the completion of the reaction, the lysing percentages were measured in accordance with the above-described 3. <Analysis Method of Lysing Percentage>. As shown in Table 4, an enzyme reaction facilitation effect was observed in sucrose fatty acid ester, polyglycerol fatty acid ester, and polysorbate emulsifiers, and a further enzyme reaction facilitation effect was obtained when existing together with sulfate salts.

TABLE 4

| emulsifier | HLB | concentration | lysing percentage (%) without addition of $(NH_4)_2SO_4$ | lysing percentage (%) addition of 1M $(NH_4)_2SO_4$ |
|---|---|---|---|---|
| without addition | — | | 33.1 | 71.8 |
| sucrose fatty acid ester | | | | |
| RYOTO Sugar Ester LWA-1570 | 15 | 1% | 66.6 | 76.1 |
| RYOTO Sugar Ester M-1695 | 16 | 1% | 61.4 | 63.0 |
| RYOTO Sugar Ester P-1570 | 15 | 1% | 62.1 | 60.7 |
| RYOTO Sugar Ester S-1570 | 15 | 1% | 47.9 | 74.4 |
| RYOTO Sugar Ester OWA-1570 | 15 | 1% | 62.1 | 74.2 |
| polyglycerol fatty acid ester | | | | |
| RYOTO Polyglyester L-7D | 16 | 1% | 51.6 | 79.8 |
| | | 0.5% | — | 83.8 |
| | | 0.25% | — | 82.9 |
| RYOTO Polyglyester M-10D | 15 | 1% | 52.1 | 79.1 |
| | | 0.5% | — | 84.5 |
| | | 0.25% | — | 81.1 |
| RYOTO Polyglyester SWA-10D | 15 | 1% | 66.0 | 81.0 |
| | | 0.5% | — | 75.5 |
| | | 0.25% | — | 70.1 |
| polysorbate | | | | |
| Tween 20 | 16.7 | 1% | 53.2 | 62.5 |
| Tween 60 | 14.7 | 1% | 50.2 | 82.0 |
| | | 0.5% | — | 83.8 |
| | | 0.25% | — | 65.6 |
| Tween 65 | 10.5 | 1% | 54.9 | 68.5 |
| Tween 80 | 15.0 | 1% | 41.9 | 72.0 |

*In the case where an emulsifier dispersed in ethanol-water is represented by the concentration of "1%" in the table, the emulsifier was added by adjusting the amount thereof such that the concentration thereof is 1% in a reaction solution.

Example 5

Effect of Additive on Various Phospholipids

Enzyme reactions by PLA1 were performed in the presence of ammonium sulfate and gum arabic by using, as a phospholipid, various phospholipids such as krill phosphatidylserine and krill phosphatidylcholine obtained in Example 1, squid phosphatidylserine and squid phosphatidylcholine prepared based on Example 1, and soybean phospholipid to mixture of phosphatidylcholine and phosphatidylethanolamine). It is to be noted that the reactions using krill phosphatidylcholine and squid phosphatidylcholine as raw materials correspond to Route 2. The lysing percentage of each reaction products was measured. According to the results shown in Table 5, a facilitation effect of additives on the enzyme reactions were recognized regardless of whether the reaction product is derived from a phospholipid containing serine or a phospholipid containing choline.

TABLE 5

| phospholipid | lysing percentage (%) without addition | lysing percentage (%) 1M $(NH_4)_2SO_4$ + 5% gum arabic |
|---|---|---|
| krill phosphatidylserine | 33.1 | 83.5 |
| krill phosphatidylcholine | 28.2 | 74.6 |
| squid phosphatidylserine | 28.8 | 63.4 |
| squid phosphatidylcholine | 30.4 | 86.4 |
| soybean phospholipid | 32.6 | 84.7 |

Example 6

Preparation and Analysis of Content of Lysophosphatidylserine 42 g of the solid matter containing phosphatidylserine obtained in Example 1 was dissolved in 800 mL of a solution containing 0.1 M acetate buffer (pH 5.5), 1 M ammonium sulfate, and 5% gum arabic; and then, 4000 units of PLA1 (manufactured by Mitsubishi Chemical Corporation) was added; and the lysing reaction was performed, while stirring, at 40° C. for 4 hours. 800 mL of hexane was added to the reaction solution, and extraction was performed. A hexane phase was collected and dried under reduced pressure by a rotary evaporator, and then, acetone precipitation treatment was performed. The obtained solid content was dissolved by a small amount of hexane and dried under reduced pressure by a rotary evaporator to obtain 19 g of a lipid containing lysophosphatidylserine. According to the result of analysis based on the above-described 2. <Analysis Method of Lysophospholipid. Content>, a lysophospholipid content of the lipid was 51.1 mass %. Furthermore, according to the result of measurement based on 1. <Analysis Method of Total Phospholipid Content>, a total phospholipid content was 69.8 mass %. Therefore, a percentage of the lysophospholipid in the total phospholipid was 73.2 mass %.

Example 7

Analysis of Content Under Each Condition

The total phospholipid content and the lysophospholipid content in the reaction product obtained under various conditions of each of Examples 2 to 6 were analyzed based on the above-descried 1. <Analysis Method of Total Phospholipid Content> and the above-described 2. <Analysis Method of Lysophospholipid Content>, respectively, and the percentage of the lysophospholipid in the total phospholipid, which is calculated from the above two values, is shown in Table 6.

TABLE 6

| salts | gums | total phospholipid content (%) | lysophospholipid content (%) | lysophospholipid/total phospholipid (%) |
|---|---|---|---|---|
| — | — | 64.5 | 16.5 | 25.6 |
| 1M $(NH_4)_2SO_4$ | — | 65.3 | 37.1 | 56.8 |
| — | 5% gum arabic | 63.9 | 25.6 | 40.1 |
| 1M $(NH_4)_2SO_4$ | 5% gum arabic | 69.8 | 51.1 | 73.2 |

Example 8

Analysis of DHA Content

In Example 5, with respect to a fatty acid part of the composition containing 2-acyl-lysophosphatidylserine obtained by allowing PLA1 to act on a fatty acid part of squid phosphatidylserine and squid phosphatidylserine in the presence of 1 M ammonium sulfate and 5% gum arabic, an analysis of a fatty acid composition was performed by gas chromatography. As shown in Table 7, compared to phosphatidylserine before the enzyme reaction by PLA1, docosahexaenoic acid (DHA) was concentrated in the composition containing 2-acyl-lysophosphatidylserine generated after the enzyme reaction.

TABLE 7

| fatty acid | before PLA1 reaction (%) | after PLA1 reaction (%) |
|---|---|---|
| C14:0 myristic acid | 1.0 | 0.3 |
| C16:0 palmitic acid | 25.6 | 9.9 |
| C16:1 palmitoleic acid | 0.5 | 0.2 |
| C18:0 stearic acid | 5.0 | 2.3 |
| C18:1 oleic acid | 1.3 | 0.6 |
| C20:5 eicosapentaenoic acid | 11.9 | 15.5 |
| C22:6 docosahexaenoic acid | 43.4 | 62.1 |
| other | 11.5 | 9.2 |

The invention claimed is:

1. A method for producing a composition containing 2-acyl-lysophosphatidylserine, the method consisting of:
   (a) obtaining a composition containing phosphatidylserine by allowing phospholipase D to act on a raw material containing phosphatidylcholine in the presence of serine to produce phosphatidylserine; and
   (b) treating the composition containing phosphatidylserine obtained in (a) with phospholipase A1 in the presence of at least one selected from each of (I), (II), and (III):
   (I) one or more salts selected from the group consisting of sulfate salts, phosphate salts, nitrate salts, citrate salts, and tartarate salts of monovalent cations,
   (II) a gum selected from the group consisting of gum arabic present in a concentration of 1 to 10%, xanthum gum present in a concentration of 0.1%, tamarind gum present in a concentration of 1 to 3%, tara gum present in a concentration of 0.5% and locust bean gum present in a concentration of 1%, and
   (III) an emulsifier
   to obtain a composition containing 2-acyl lysophosphatidylserine containing 26% to 51% by mass of a lysophospholipid per solid content.

2. A method for producing a composition containing 2-acyl-lysophosphatidylserine, consisting of:
   (c) obtaining a composition containing 2-acyl-lysophosphatidylcholine by allowing phospholipase A1 to act on a raw material containing phosphatidylcholine in the presence of at least one selected from each of (I), (II), and (III):
   (I) one or more salts selected from the group consisting of sulfate salts, phosphate salts, nitrate salts, citrate salts, and tartarate salts of monovalent cations,
   (II) a gum selected from the group consisting of gum arabic present in a concentration of 1 to 10%, xanthum gum present in a concentration of 0.1%, tamarind gum present in a concentration of 1 to 3%, tara gum present in a concentration of 0.5% and locust bean gum present in a concentration of 1%, and
   (III) an emulsifier
   to produce 2-acyl-lysophosphatidylcholine; and
   (d) treating the composition containing 2-acyl-lysophosphatidylcholine obtained in (c) with phosphaliase D in the presence of serine to produce a composition containing 2-acyl-lysophosphatidylserine containing 26% to 51% by mass of a lysophospholipid per solid content.

3. The producing method according to claim 1, wherein the treating step (b) is carried out in the presence of at least the one or more salts of monovalent cations, wherein a concentration of the one or more salts of monovalent cations is 0.25 to 2.0 M.

4. The producing method according to claim 2, wherein the treating step (c) is carried out in the presence of at least the one or more salts of monovalent cations, wherein a concentration of the one or more salts of monovalent cations is 0.25 to 2.0 M.

5. The producing method according to claim 1, wherein the treating step (b) is carried out in the presence of at least the one or more salts of monovalent cations, and the one or more salts of the cations is ammonium sulfate and/or sodium sulfate.

6. The producing method according to claim 2, wherein the treating step (c) is carried out in the presence of at least the one or more salts of monovalent cations, and the one or more salts of the cations is ammonium sulfate and/or sodium sulfate.

7. The producing method according to claim 1, wherein the treating step (b) is carried out in the presence of at least the emulsifier, wherein the emulsifier is one or more selected from the group consisting of sucrose fatty acid ester emulsifiers, polyglycerol fatty acid ester emulsifiers, and polysorbate emulsifiers.

8. The producing method according to claim 2, wherein the treating step (c) is carried out in the presence of at least the emulsifier, wherein the emulsifier is one or more selected from the group consisting of sucrose fatty acid ester emulsifiers, polyglycerol fatty acid ester emulsifiers, and polysorbate emulsifiers.

9. The producing method according to claim 1, wherein the raw material containing phosphatidylcholine is derived from marine and/or plant.

10. The producing method according to claim 2, wherein the raw material containing phosphatidylcholine is derived from marine and/or plant.

11. The producing method according to claim 1, wherein the raw material containing phosphatidylcholine is derived from marine.

12. The producing method according to claim 2, wherein the raw material containing phosphatidylcholine is derived from marine.

13. The method according to claim 1, wherein the percentage of the lysophospholipid in the total phospholipid in the composition containing 2-acyl-lysophosphatidylserine is 40% to 73% by mass.

14. The method according to claim 2, wherein the percentage of the lysophospholipid in the total phospholipid in the composition containing 2-acyl-lysophosphatidylserine is 40% to 73% by mass.

\* \* \* \* \*